| United States Patent [19] | [11] Patent Number: 5,004,569 |
| Meier et al. | [45] Date of Patent: Apr. 2, 1991 |

[54] PROCESS FOR THE PRODUCTION OF CARBOXYLIC ACID ESTERS

[75] Inventors: Helmut-Martin Meier, Ratingen; Klaus Kircher, Leverkusen; Klaus Berg, Krefeld, all of Fed. Rep. of Germany

[73] Assignee: Bayer Aktiengesellschaft, Leverkusen-Bayerwerk, Fed. Rep. of Germany

[21] Appl. No.: 281,887

[22] Filed: Dec. 6, 1988

Related U.S. Application Data

[63] Continuation of Ser. No. 45,399, May 4, 1987, abandoned.

[30] Foreign Application Priority Data

May 14, 1986 [DE] Fed. Rep. of Germany ....... 3616137

[51] Int. Cl.$^5$ .......................... C09F 5/08; C11C 3/00; C11C 3/02

[52] U.S. Cl. ................................ 260/410.6; 260/410.5; 260/410.7; 260/410.9 R; 260/408; 560/89; 560/98; 560/105; 560/112; 560/122; 560/179; 560/192; 560/198; 560/204; 560/227; 560/254; 560/264; 560/265; 560/263; 560/266

[58] Field of Search ...................... 260/410.9 R, 410.5, 260/410.6, 410.7, 408; 560/264, 265, 263, 254, 266, 105, 112, 98, 89, 122, 227, 179, 198, 204, 192

[56] References Cited

U.S. PATENT DOCUMENTS 2,622,071 12/1952 Harrison ............................. 560/140

*Primary Examiner*—Paul J. Killos
*Attorney, Agent, or Firm*—Connolly and Hutz

[57] ABSTRACT

The invention relates to a process for the production of carboxylic acid esters from carboxylic acids and alcohols which is characterized in that neutral phosphites containing oxetane groups are used as esterification catalysts.

2 Claims, No Drawings

PROCESS FOR THE PRODUCTION OF CARBOXYLIC ACID ESTERS

This application is a continuation, of application Ser. No. 045,399, filed May 4, 1987, now abandoned.

This invention relates to the use of neutral Phosphites containing oxetane groups for the production of carboxylic acid esters from carboxylic acids and alcohols.

It is already known that glycerol and fatty acids can be reacted in the presence of metal oxides or metals, such as zinc oxide or tin (DRP 403 644). According to Houben-Weyl, "Methoden der Organischen Chemie", Sauerstoffverbindungen III, Vol. VIII, 1952, pages 516 et seq., more especially page 517, it is also common practice to use mineral acids, such as hydrochloric acid, sulfuric acid, phosphoric acid, or organic acids, such as aromatic sulfonic acid, or acidic salts as esterification catalysts. US-PS 4 526 725 describes the esterification of carboxylic acids or carboxylic acid anhydrides with alcohols in the presence of an alkoxy-titanium compound modified with bis-hydroxyethyl amine. $\chi$-Hydroxyalkyl phosphites are known as anti-yellowing reagents in coating compositions (DE-PS 3 422 668).

In addition, EP 0 158 501 describes a process for the production of polyesters in the presence of phosphonites. Finally, DOS 3 516 776 describes a process for the production of colophony-pentaerythritol esters in the presence of phosphinic acid.

The esterification processes described in DRP 403 644 and in US-PS 4 526 725 give an end product having a high OH number which, on account of its metal content, cannot be used as an additive in a transparent plastics material, because corresponding products are clouded.

The process proposed in Houben-Weyl, loc. cit., gives esters which have an excessively high acid number in the end product and which can lead to troublesome secondary reactions when used as an additive in certain plastics. In addition, the natural color of the esters obtained with these esterification catalysts are too dark for use as an additive in light or colorless plastic moldings.

According to the U.S. Pat. No. 2 622 071 and U.S. Pat. No. 2 676 158 phenolic OH-groups have been esterified with organic carboxylic acids by using aliphatic respectively aromatic phosphites.

The phosphorus-containing compounds described in DE-P 3 422 68, in EP0 158 501 and in DOS 3 516 776 are not suitable esterification catalysts, as the Comparison Examples show, because they do not help in obviating the disadvantages described above.

It has now surprisingly been found that these disadvantages can be obviated by carrying out the esterification in the presence of neutral phosphites containing oxetane groups.

Suitable neutral phosphites containing oxetane groups are, for example, compounds corresponding to the following formula

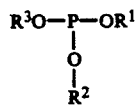

in which at least one of the substituents $R^1$, $R^2$ and $R^3$ is the residue of a monoalcohol containing oxetane groups, while at most 2 of the substituents $R^1$, $R^2$ and $R^3$ are residues of primary, secondary or tertiary aliphatic, cycloaliphatic or heterocyclic monoalcohols free from oxetane groups or monohydroxyaryls free from oxetane groups.

Preferred monoalcohols containing oxetane groups are those corresponding to the following formula

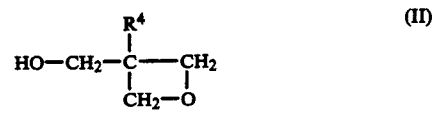

in which $R^4$ represents H, $C_1$-$C_{18}$ alkyl, $C_3$-$C_{12}$ cycloalkyl, optionally alkyl-substituted $C_6$-$C_{14}$ aryl, $C_7$-$C_{18}$ aralkyl or —$CH_2$—O—R, where R may again be the alkyl, cycloalkyl, aryl and aralkyl radicals mentioned for $R^4$. $R^4$ is preferably a $C_1$-$C_5$ alkyl radical.

Suitable monoalcohols containing oxetane groups of formula (II) are, for example, 3-hydroxymethyl oxetane, 3-methyl-3-hydroxymethyl oxetane, 3-ethyl-3-hydroxymethyl oxetane, 3-pentyl-3-hydroxymethyl oxetane, 3-hexadecyl-3-hydroxymethyl oxetane, 3-octadecyl-3-hydroxymethyl oxetane, 3-cyclohexyl-3-hydroxymethyl oxetane, 3-phenyl-3-hydroxymethyl oxetane, 3-p-tolyl-3-hydroxymethyl oxetane, 3-benzyl-3-hydroxymethyl oxetane, 3-methoxymethyl-3-hydroxymeth oxetane, 3-ethoxymethyl oxetane, 3-octadecyl-methyl3-hydroxymethyl oxetane, 3-phenoxymethyl-3-hydroxymethyl oxetane, 3-p-tolyloxymethyl-3-hydroxymethyl oxetane and 3-benzyloxymethyl-3-hydroxymethyl oxetane.

Other suitable monoalcohols containing oxetane groups which do not correspond to formula (II) are, for example, 3-phenoxy-3-hydroxymethyl oxetane, 3-p-chloro-phenoxy-3-hydroxymethyl oxetane, 3-p-tert.-butylphenoxy3-hydroxymethyl oxetane, 3-acetyloxymethyl-3-hydroxymethyl oxetane and 3-stearoyloxymethyl-3-hydroxymethyl oxetane.

Suitable monoalcohols and monohydroxyaryls free from oxetane groups for the production of the phosphorous acid esters corresponding to formula (I) are, for example, primary aliphatic $C_1$-$C_{18}$ monoalcohols free from oxetane groups, secondary aliphatic $C_3$-$C_{18}$ monoalcohols free from oxetane groups and tertiary aliphatic $C_4$-$C_{18}$ monoalcohols free from oxetane groups; also suitable are, for example, secondary, cycloaliphatic $C_3$-$C_{12}$ monoalcohols free from oxetane groups, primary cycloaliphatic $C_4$-$C_{12}$ monoalcohols free from oxetane groups or tertiary cycloaliphatic $C_4$-$C_{12}$ monoalcohols free from oxetane groups; also suitable are, for example, primary, secondary or tertiary heterocyclic $C_3$-$C_{12}$ monoalcohols free from oxetane groups.

Suitable monohydroxy compounds free from oxetane groups are, for example, methyl alcohol, ethyl alcohol, N-propyl alcohol, isopropyl alcohol, N-butyl alcohol, isobutyl alcohol, tert.-butyl alcohol, n-hexyl alcohol, 2-ethyl-1-hexanol, decyl alcohol, lauryl alcohol, octadecyl alcohol, S-ethylene thioglycol, S-dodecyl thioglycol, cyclohexyl alcohol, 2-methyl cyclohexyl alcohol, cyclobutanol, cyclopropanol, benzyl alcohol, $\alpha$-methyl benzyl alcohol, tetrahydrofurfuryl alcohol, 5-hydroxymethyl-5-ethyl-1, 3-dioxane, ethylene glycol monobutyl ester, diacetin, trimethylol propane diallyl ether, phenol, 2,6-diisobutyl-p-methyl phenol, $\alpha$-naphthol, $\beta$-naphthol and p-chlorophenol.

Phosphorous acid esters containing oxetane groups of formula (I) which may be used in accordance with the invention are, for example, tris-(2, 2-dimethylene oxide butyl)-phosphite, bis-(2, 2-dimethylene oxide butyl)-phenyl phosphite, 2, 2-dimethylene oxide butyl-bis-(phenyl)phosphite, bis-(2, 2-dimethylene oxide butyl)-decyl phosphite, bis-(2, 2-dimethylene oxide butyl)-p-tolyl phosphite, 2, 2-dimethylene oxide-butyl-bis-(o-chlorophenyl)-phosphite, bis-(2, 2-dimethylene oxide-butyl)-benzyl phosphite, bis-(2, 2-dimethylene oxide-butyl)-octadecyl phosphite, bis(2, 2-dimethylene oxide-butyl)-methyl phosphite, bis(2, 2-dimethylene oxide-butyl)-cyclohexyl phosphite, 2, 2dimethylene oxide-butyl-bis-(decyl)-phosphite, tris(2, 2-dimethylene oxide-propyl)-phosphite, bis-(2, 2-dimethylene oxide-propyl)-phenyl phosphite, 2, 2-dimethylene oxide-propyl-bis-(phenyl)-phosphite, tris-(2, 2-dimethylene oxide-octadecyl)-phosphite, tris-(2, 2-dimethylene oxide 2-phenyl ethyl)-phosphite, bis-(2, 2-dimethylene oxide-2phenyl ethyl)-phenyl phosphite, tris-(2, 2-dimethylene oxide-2-p-tolyl ethyl)-phosphite, tris-(2, 2-dimethylene oxide-3-phenyl propyl)-phosphite, tris-(2, 2-dimethylene oxide-3-methoxypropyl)-phosphite, tris-(2, 2-dimethylene oxide-3-ethoxypropyl)-phosphite, tris-(2, 2-dimethylene oxide-3-butoxypropyl)-phosphite, tris-(2, 2-dimethylene oxide-3-octadecyloxypropyl)-phosphite, tris-(2, 2-dimethylene oxide-3-phenoxypropyl)-phosphite and tris-(2, 2dimethylene oxide-3-benzyloxypropyl)-phosphite.

Phosphorous acid esters suitable for use in accordance with the invention are also those of polyalcohols containing oxetane groups, more especially dialcohols containing oxetane groups.

The phosphorous acid esters of dialcohols containing oxetane groups, correspond to the following structural formulae:

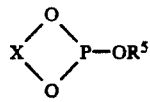
(IIIa)

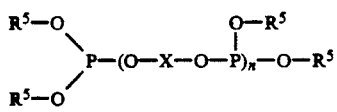
(IIIb)

in which X is the residue of a dialcohol containing oxetane groups HO-X-OH with X as an organic residue containing oxetane groups and, for example, from 5 to 20 carbon atoms, $R^5$ is the residue of a monoalcohol free from oxetane groups or of a monohydroxyaryl free from oxetane groups and "n" is an integer of from 1 to 10 inclusive, preferably of from 1 to 3 inclusive and more especially 1 or 2.

Suitable monoalcohols $R^5$—OH free fromoxetane groups and monohydroxy aryls $R^5$—OH free from oxetane groups are those already mentioned in the characterization of the phosphorous acid esters (I).

Examples of dialcohols HO-X-OH containing oxetane groups are

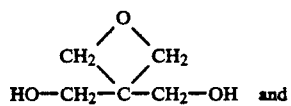
and

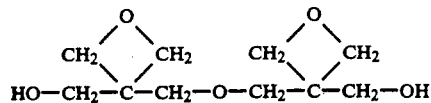

Examples of phosphorous acid esters corresponding to formula (IIIa) or (IIIb) are

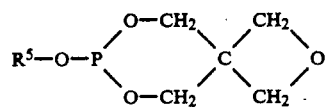

and

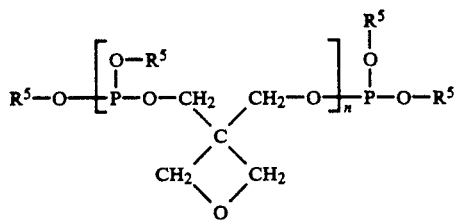

in which $R^5$ and "n" have the meanings defined for structural formulae (IIIa) and (IIIb).

Other phosphorous acid esters suitable for use in accordance with the invention are those of monoalcohols containing oxetane groups and aliphatic, cycloaliphatic or heterocyclic polyalcohols, preferably dialcohols, free from oxetane groups and/or polyhydroxyaryls, preferably dihydroxyaryls, free from oxetane groups.

Examples of polyalcohols free from oxetane groups are those containing from 2 to 20 carbon atoms, such as for example ethylene glycol, 1, 2-propanediol, 2, 2-dimethyl propanediol, 2-methylene-1,3-propanediol, 2,2-dimethyl-4, 4-dimethyl-1, 3-cyclobutanediol, glycerol, trimethylol propane, pentaerythritol, sorbitol, thiodiglycol, diethylene glycol, triethylene glycol, 2-ethyl1, 3-propanediol, 1, 4-butanediol, 1, 4-butene-2-diol, 1, 6-n-hexanediol, 4, 4'-bis-hydroxycyclohexyl-2, 2-propane, cyclohexyl-1, 4-dimethanol and 1, 3-hydroxy-2, 2, 4, 4-tetramethyl cyclobutane.

Polyhydroxyaryls free from oxetane groups are, for example, those containing from 6 to 30 carbon atoms, such as for example hydroquinone, resorcinol, pyrocatechol, di-t-butyl pyrocatechol, 4, 4'-dihydroxydiphenyl, bis-(hydroxyphenyl)-alkanes such as, for example, $C_1$-$C_8$ alkylene and $C_2$-$C_8$ alkylidene bisphenols, bis-(hydroxy-phenyl)-cycloalkanes, such as for example $C_5$-$C_{15}$ cycloalky and $C_5$-$C_{15}$ cycloalkylidene bisphenols, α, α'-bis-(hydroxyphenyl)-diisopropyl benzene and the corresponding nucleus-alkylated and nucleus-halogenated compounds, for example bis-(4-hydroxyphenyl)-2, 2-propane (bisphenol A), bis-(4-hydroxy-3, 5-dichlorophenyl)-2, 2propane (tetrachlorobisphenol A), bis-(4-hydroxy-3, 5-dibromophenyl)-2,2-propane (tetrabromobisphenol A), bis-(4-hydroxy-3, 5-dimethylphenyl)-2, 2-propane (tetramethylbisphenol A), bis-(4-hydroxyphenyl)-1, 1-cyclohexane (bisphenol Z) and also α, α'-bis-(4-hydroxyphenyl)-p-diisopropyl benzene, dihydronaphthalenes, dihydroxy anthracenes, phloroglucinol, pyrogallol, bis-(2-hydroxy3-tert.-butyl phenyl)-methane, bis-(2-hydroxy-3-cyclole hexyl phenyl)- sulfide, bis-(2-hydroxy-3-methyl phenyl)ether and bis-(2-hydroxy-3-tert.-butyl-5-methyl phenyl)2,2-propane.
Phosphorous acid esters containing oxetane groups with polyalcohols free from oxetane groups are, for example,
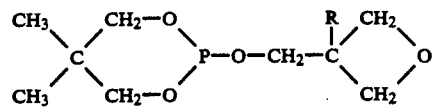
(with R for example H or $C_1$–$C_{18}$ alkyl),
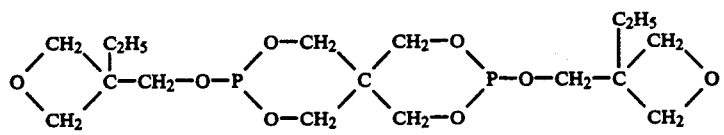
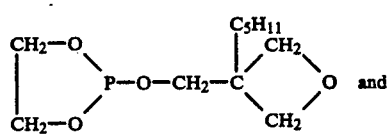 and
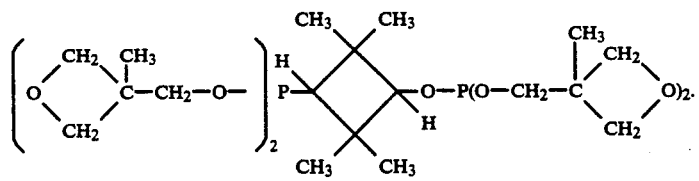
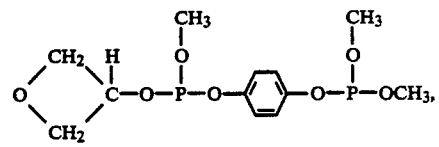
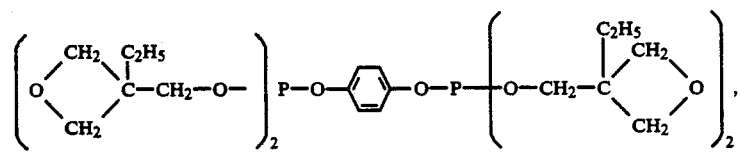
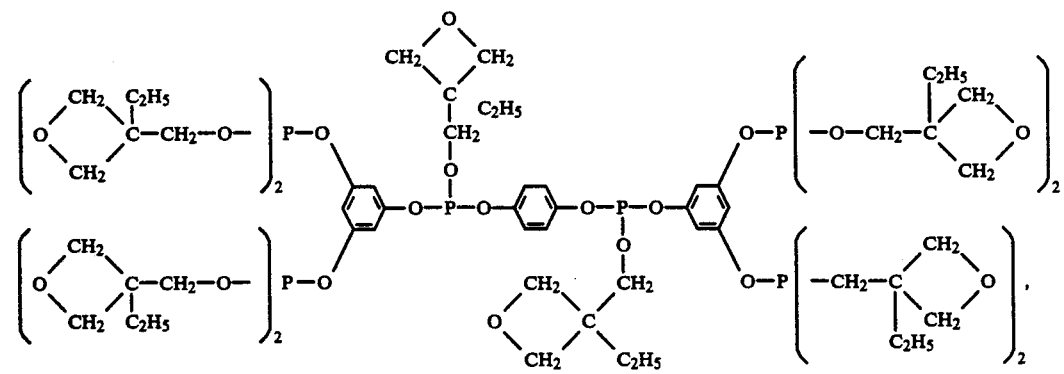
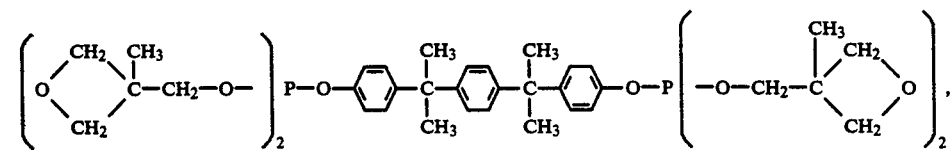

-continued
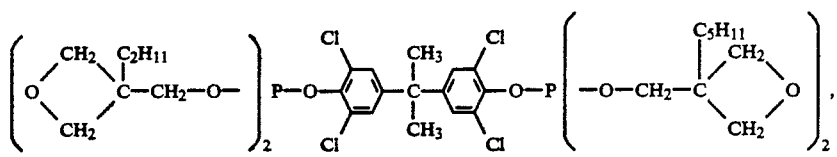
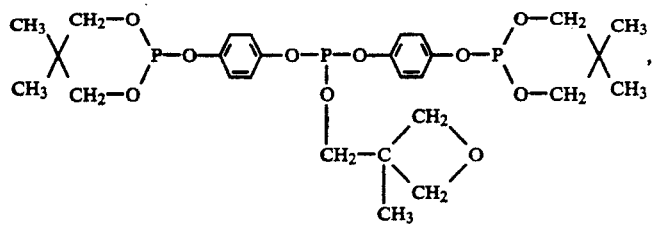
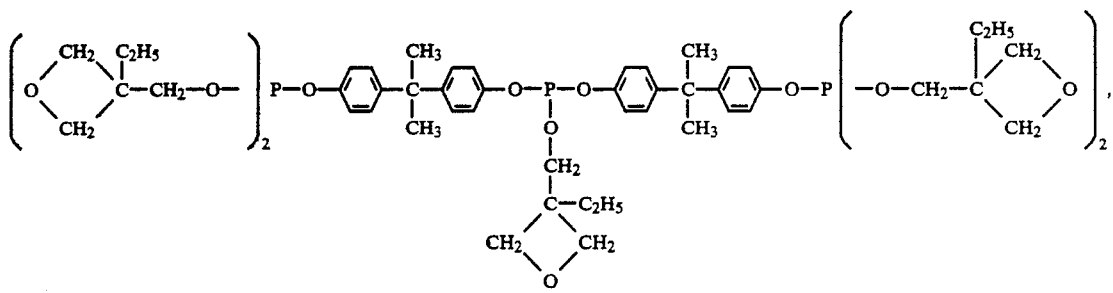
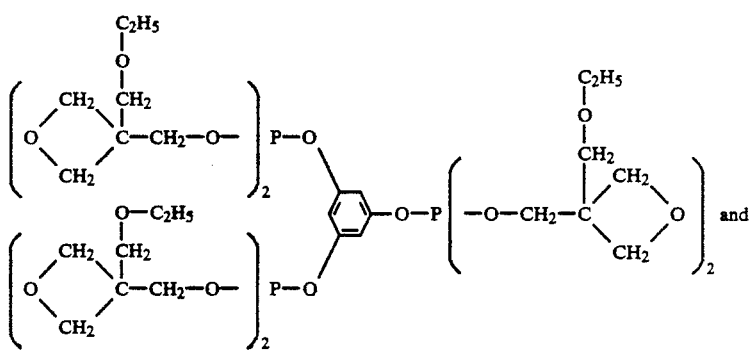
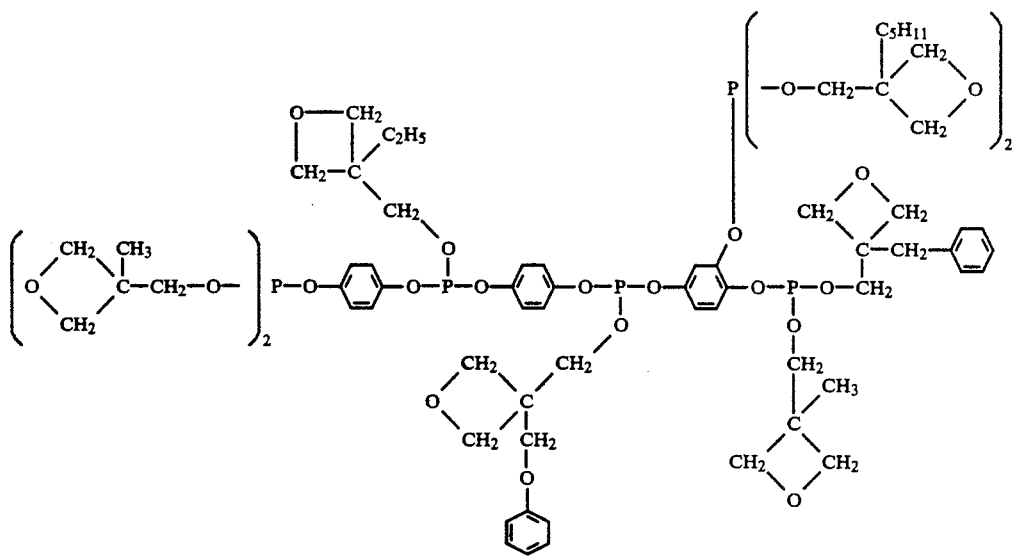
In addition to monoalcohols containing oxetane groups, monoalcohols free from oxetane groups and/or monohydroxyaryls free from oxetane groups may be incorporated in the above-mentioned phosphorous acid esters containing oxetane groups with polyalcohols and/or polyhydroxyaryls free from oxetane groups suitable for use in accordance with the invention.

Finally, other phosphorous acid esters suitable for use in accordance with the invention are those of monoalcohols containing oxetane groups and monoalcohols free from oxetane groups and/or monohydroxyaryls free from oxetane groups and/or polyalcohols free from oxetane groups and/or polyhydroxyaryls free from oxetane groups.

The phosphorous acid esters containing oxetane groups suitable for use in accordance with the invention may be used either individually or in admixture with one another.

A particularly preferred phosphorous acid ester is tris-(2, 2-dimethylene oxide-butyl)-phosphite

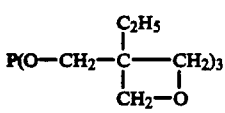

The phosphorous acid esters containing oxetane groups corresponding to formulae (I), (IIIa) and (IIIb) are obtained in known manner by transesterification of the corresponding alcohols or phenols containing oxetane groups with trialkyl or trialkyl phosphites or by reaction of phosphorus trichloride with the corresponding alcohols or phenols, optionally in admixture with other alcohols or phenols free from oxetane groups, in the presence of acid-binding agents, for example in accordance with US-PS 3 209 013.

Phosphites containing oxetane groups of the type in question are also described in German patents 2 140 207 (Le A 13 917) and 2 255 639 (Le A 14 709) where they are used for the stabilization of thermoplastic aromatic polycarbonates.

The neutral phosphites containing oxetane groups used as esterification catalysts may be added in quantities of from 0.01 to 10% by weight and preferably in quantities of from 0.1 to 5% by weight, based on the total weight of the carboxylic acid and alcohol. The esterification catalysts may be added to the reaction mixture in various forms. They may be added to the reaction mixture either in liquid or in solid form; initially introduced in the form of a solution in one of the starting products or added to the reaction mixture during the reaction. The esterification catalysts are preferably introduced together with the starting products.

Accordingly, the present invention also relates to a process for the production of carboxylic acid esters from carboxylic acids and' alcohols by the known methods of melt condensation, azeotropic esterification or extractive esterification, characterized in that neutral phosphites containing oxetane groups are used as esterification catalysts in quantities of from 0.01 to 5% by weight, based on the total weight of carboxylic acid and alcohol.

The melt condensation process is characterized in that the starting components are heated to the reaction temperature in liquid or molten form. Water is eliminated, optionally with passage of an inert gas. The esterification reaction is over when no more water of reaction is formed.

The azeotropic esterification process is characterized in that the esterification is carried out in a solvent which forms an azeotrope with water. In this case, the water of reaction formed is removed from the reaction mixture by azeotropic distillation.

The extractive esterification process is characterized in that the ester formed is dissolved out from the reaction mixture by a solvent. The solvent itself should dissolve only slightly in water.

(For a detailed description of these three processes, see "Organikum", 12th Edition, NEB, Deutscher Verlag der Wissenschaften, Berlin 1973, pages 441 et seq. and also Houben-Weyl, "Methoden der Organischen Chemie", Sauerstoffverbindungen III, Vol. VIII, 1952, pages 516 to 526, loc. cit.).

Suitable carboxylic acids which may be esterified by the process according to the invention are those corresponding to the following formula $$R^6 (CO_2H)_n \text{ (IV)}$$

in which n is an integer of from 1 to 6 and R is the n-bonded residue of linear or branched alkanes which may contain ether bridges, cycloalkanes, aryl alkanes or arenes which may additionally be substituted by fluorine. R may also be hydrogen. Preferred C-substituents $R^6$ are $C_1$–$C_{30}$ chains or rings of aliphatic or aromatic structure.

Suitable acids of formula (IV) are, for example, formic acid, acetic acid, propionic acid, butyric acid, isobutyric acid, pentanoic acid, 2, 2-dimethyl propanoic acid, 2-ethyl hexanoic acid, coconut oil fatty acid, lauric acid, myristic acid, palmitic acid, stearic acid, eicosanoic acid, behenic acid, lignoceric acid, sebacic acid, undecane diacid, dodecane diacid, brassylic acid, thapsic acid, butane tetracarboxylic acid, naphthenic acid, hexahydrobenzoic acid, benzoic acid, phenyl acetic acid, 4-tert.-butyl benzoic acid, hexahydroterephthalic acid, phthalic acid, cyclopentane tetracarboxylic acid, 4-phenyl phthalic acid, diglycolic acid, ethyl glycolic acid, trifluoroacetic acid, perfluorobenzoic acid, 3, 4-bis-(trifluoromethyl)-benzoic acid, p-trifluoromethyl phenyl acetic acid, nonadecafluorodecanoic acid, octafluoroadipic acid, 2H,2H-heptadecafluorodecanoic acid, H,3H-hexafluoroadipic acid, perfluoroglutaric acid and perfluorooctanoic acid.

Suitable alcohols which may be esterified by the process according to the invention are those corresponding to the following formula $$(R^7)_n-C(CH_2OH)_{4-n} \text{ (V)}$$

in which n =0 or 1 or 2 or 3 and $R^7$ may be hydrogen, linear or branched alkyl, cycloalkyl, alkoxy, aralkyl or aryl; where n =2 or 3, $R^7$ may be the same or different.

In addition, the substituents $R^7$ may be substituted by fluorine.

Preferred C-substituents $R^7$ are $C_1$–$C_{30}$ chains or rings of aliphatic or aromatic structure.

Suitable alcohols corresponding to formula (V) are pentaerythritol, glycerol, trimethylol ethane, trimethylol propane, trimethylol hexane, trimethylol octadecane, 1,3-propanediol, neopentyl glycol, 2-methyl-2-propyl-1,3propanediol, 2,2-diethyl-1, 3-propanediol, 1, 4-cyclohexane dimethylol, bis-methylol tricyclodecane, 1, 1-cyclohexane dimethylol, ethanol, propanol, neopentyl alcohol, 2-ethyl1-butanol, trimethyl-1-hexanol, stearyl alcohol, 2-methoxy ethanol, 2-propoxy ethanol, 2-(2-butoxy ethoxy)-ethanol, 2, 2, 2-trifluoroethanol, 1, 3-difluoro-4-methylol benzene, 1-trifluoromethyl-4-methylol benzene, 1, 2, 4, 5-tetrafluoro3-trifluoromethyl-6-methylol benzene, 1, 1, 1-trifluoro-nonan-9-ol, 1H,1H,1H-2, 2, 3, 3, 4, 4-hexafluoro-1, 5-pentadi pentafluorobenzyl alcohol.

Alcohols containing from 4 to 6 OH groups, such as for example arabitol, adonitol, mannitol, dulcitol, xylitol, sorbitol, may also be used for the process according to the invention.

In a general embodiment, the starting components are initially introduced either together or separately in succession in solid form, molten form or dissolved in a suitable solvent. The molar ratio of $CO_2$ groups to —OH groups may be from 0.5 to 2 and preferably from 0.8 to 1.2. The esterification may take place in an inert gas atmosphere at 170 to 280° C and preferably at 200° to 250° C. or in a solvent at a suitable temperature. The esterification is over when the necessary quantity of water has been separated or when an acid number or hydroxyl number of <10 mg KOH/g has been reached.

A special embodiment is described in the Examples.

13 461), DE-OS 2 220 185 (Le A 14 329), DE-OS 2 507 748 (Le A 16 284) and DE-OS 2 729 485.

The effectiveness of the process according to the invention is illustrated by the following Examples and Comparison tests.

General procedure 1.1 mole stearic acid, 0.25 mole pentaerythritol, 2.5 g catalyst are fused under nitrogen at 200° C. in a 2-liter three-necked glass apparatus with a descending condenser and the resulting melt stirred at that temperature until 18 ml $H_2O$ (1 mole) have separated. The time taken to reach the end of the reaction and the acid numbers and hydroxyl numbers obtained are shown in the following Table in dependence upon various catalysts. The acid number and hydroxyl number are determined in accordance with DIN 53 402 or in accordance with P.H. Selden, "Glasfaserverstarkte Kunststoffe", p. 444 (1967).

| No. | Catalyst | Elimination of 1 mole $H_2O$ after (h) | Acid no. mg KOH/g | OH no. mg KOH/g | Color |
|---|---|---|---|---|---|
| 1 | [structure] | 8 | 37 | 73 | dark brown |
| 2 | [structure] | 8 | 27 | 37 | " |
| 3 | $H_3PO_3$ | 32 | 27 | 4 | " |
| 4 | $(HO-CH_2)_3P$ | 24 | 23 | 15 | " |
| 5 | $(C_4H_9O)_4Ti$ | 40 | 20 | 6 | " |
| 6 | [structure with $C_2H_5$] | 64 | 14 | 15 | yellow |
| 7 | — | 24 | 19 | 21 | yellow |
| 8 | $P(OCH_2-C(C_2H_5)-O)_3$ | 6 | 14 | 6,8 | white |
| 9 | [structure] | 7 | 11 | 6 | white |

The esters obtained may also be purified by fractional crystallization or distillation after their preparation.

A major and surprising advantage of the process according to the invention is the relatively rapid esterification for low OH and acid numbers of the product formed, as shown in the Examples.

The carboxylic acid esters obtained are generally known compounds. They may be thermally used in known manner partly as solvents or as intermediate products for organic syntheses.

Some of the carboxylic acid esters obtainable by the process according to the invention are particularly suitable as mold release agents for thermoplastic aromatic polycarbonates according to DE-OS 2 0654 095 (Le A

We claim:

1. A process for the production of a carboxylic acid ester, which comprises reacting a carboxylic acid with an alcohol in the presence, as an esterification catalyst, of a neutral phosphite compound which is a phosphorous acid ester of at least one monoalcohol containing at lease one oxetane group and at least one polyhydroxy compound selected from the group consisting of an aliphatic polyalcohol free of oxetane groups, a cycloaliphatic polyalcohol free of oxetane groups and a polyhydroxyaryl compound free of oxetane groups.

2. A process for the production of a carboxylic acid ester which comprises reacting a carboxylic acid with an alcohol in the presence as an esterification catalyst of a neutral phosphite of the formula (I)

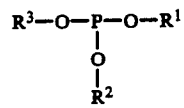

wherein i) at least one of $R^1$, $R^2$, $R^3$ is the residue of a monoalcohol containing oxetane groups and ii) at most two of $R^1$, $R^2$ and $R^3$ are primary, secondary or tertiary aliphatic or cycloaliphatic alcohol residues which are free from oxetane groups or monohydroxyaryl groups which are free from oxetane groups.

* * * * *